(12) United States Patent
Guliashvili et al.

(10) Patent No.: US 8,858,803 B2
(45) Date of Patent: Oct. 14, 2014

(54) METHODS OF PREPARING NOVEL HALIDE ANION FREE QUATERNARY AMMONIUM SALT MONOMERS, POLYMERIZATION METHODS THEREFOR, AND METHODS OF USE OF THE RESULTING POLYMERS

(75) Inventors: Tamaz Guliashvili, Philadelphia, PA (US); Stephen R. Vasconcellos, Doylestown, PA (US)

(73) Assignee: General Electric Company, Schenectady, NY (US)

( * ) Notice: Subject to any disclaimer, the term of this patent is extended or adjusted under 35 U.S.C. 154(b) by 774 days.

(21) Appl. No.: 12/951,769

(22) Filed: Nov. 22, 2010

(65) Prior Publication Data
US 2012/0125863 A1    May 24, 2012

(51) Int. Cl.
| | | |
|---|---|---|
| *C02F 1/56* | (2006.01) |
| *C07C 211/63* | (2006.01) |
| *C08F 126/04* | (2006.01) |
| *C07C 209/68* | (2006.01) |
| *C07C 213/08* | (2006.01) |

(52) U.S. Cl.
CPC .............. *C08F 126/04* (2013.01); *C07C 211/63* (2013.01); *C02F 1/56* (2013.01); *C07C 209/68* (2013.01); *C07C 213/08* (2013.01)
USPC .......................................... 210/736; 210/732

(58) Field of Classification Search
CPC ................................ C02F 1/52; C02F 1/5272
USPC ........................................................ 210/735
See application file for complete search history.

(56) References Cited

U.S. PATENT DOCUMENTS

| | | |
|---|---|---|
| 3,288,770 A | 11/1966 | Butler |
| 4,064,333 A | 12/1977 | Rabinowitz et al. |
| 4,452,957 A | 6/1984 | Neigel |
| 4,715,962 A | 12/1987 | Bhattacharyya et al. |
| 4,784,776 A | 11/1988 | Mangravite, Jr. |
| 5,422,408 A | 6/1995 | Cramm et al. |
| 2008/0179188 A1 | 7/2008 | Nelson et al. |
| 2010/0006511 A1 | 1/2010 | Walterick, Jr. et al. |

FOREIGN PATENT DOCUMENTS

| | | |
|---|---|---|
| EP | 1491352 A2 | 12/2004 |
| WO | WO96/35731 A1 | 11/1996 |
| WO | 2007079069 A1 | 7/2007 |
| WO | WO2008/079652 A1 | 7/2008 |

OTHER PUBLICATIONS

Paola Cardiano et al; "A new application of ionic liquids: hydrophobic properties of tetraalkylammonium-based poly(ionic liquid)s", Journal of Materials Chemistry, Jan. 1, 2008, p. 1253-1254, vol. 18, No. 11.
WO Search Report and Written Opinion from Application No. PCT/US2011/060906 dated May 18, 2012.

*Primary Examiner* — Tony G Soohoo
*Assistant Examiner* — Peter Keyworth
(74) *Attorney, Agent, or Firm* — Wegman, Hessler & Vanderburg

(57) ABSTRACT

Methods are provided for making halide-free quaternary ammonium salt monomers. Polymers prepared from the monomers and methods of using the polymers to clarify raw, untreated water or wastewater are also disclosed.

8 Claims, No Drawings

METHODS OF PREPARING NOVEL HALIDE ANION FREE QUATERNARY AMMONIUM SALT MONOMERS, POLYMERIZATION METHODS THEREFOR, AND METHODS OF USE OF THE RESULTING POLYMERS

FIELD OF USE

The present invention pertains to methods for making chloride free Quaternary Ammonium Salt Monomers, Polymers prepared from the Monomers, and Methods of Using the Polymers in water treatment processes such as for use as flocculants and coagulants in water treatment.

BACKGROUND OF THE INVENTION

Water clarification is well known throughout a number of industries. Various physical means have been used to remove particulate matter dispersed in a bulk liquid phase. Examples of common particulate separation techniques include filtration, settling, desalting, electrochemical techniques, centrifugation, flotation, and the like. Such separation processes can often be made more efficient by the use of coagulating and flocculating agents.

Coagulation may be defined as the stabilization of colloids by neutralizing the forces that keep the colloidal particles dispersed or separated from each other in the wastewater. Cationic coagulants are often used to provide positive electrical charges to the colloidal particles to neutralize the negative charge on the particles. As a result, the particles collide to form larger particles called flocs. Flocculation, on the other hand, refers to the action of polymeric treatments in the formation of bridges between the flocs to thereby form large agglomerates or clumps. Anionic and cationic polymers are commonly employed as flocculants to agglomerate the flocs so that the agglomerates will float and not settle. Once suspended in the wastewater, they can be removed via sedimentation, filtration, or other separation techniques.

Commonly employed cationic coagulants such as those based on polydiallyldimethylammonium chloride (PDADMAC) are disclosed for example in U.S. Pat. No. 3,288,770. Additionally, cationic copolymers such as those based on acrylamide copolymers with cationic repeat units such as quaternary ammonium acrylates dimethylaminoethylacrylate methyl chloride (AETAC) or dimethylaminoethylmethacrylate methyl chloride (METAC) are often used.

In those situations in which quaternary ammonium salt moieties are present in polymers that are employed as cationic coagulants, the anionic counter ion to the cationic nitrogen is often a chloride ion. These chloride ions are corrosive, and when excessive amounts of same are found in the wastewater, corrosion of metal surfaces in contact with the water can occur.

Additionally, environmentally based requests to limit the amount of total dissolved solids (TDS) present in effluents have been increasing over the years. Inorganic ions that are measured as part of the TDS discharge include chloride ions. Many industries and municipal wastewater facilities must comply then with new TDS standards; thus raising concern for chloride content in such discharge. TDS also presents an issue for water reuse of treated wastewater.

SUMMARY OF THE INVENTION

In one exemplary embodiment, a method is provided for forming diallyldialkylammonium anion monomer wherein diallyldialkylammonium chloride is reacted with an anion contributing metathesis agent in an aqueous solution to yield a precipitate and diallyldimethylammonium anion. The method further comprises removing the precipitate from solution. In accordance with another aspect of the invention, the anion contributing metathesis agent is a member selected from the group consisting of potassium acetate, potassium methanesulfonate, and potassium acrylate. In accordance with another exemplary embodiment, the precipitate is potassium chloride.

In another embodiment, a non-chloride containing quaternary ammonium salt anion monomer is formed from a quaternary ammonium salt chloride precursor. The method comprises reacting the precursor with an anion metathesis agent in an aqueous medium to yield a precipitate and the non-chloride containing quaternary ammonium salt anion monomer. The precipitate is then removed from the reaction medium.

In another embodiment, the quaternary ammonium salt chloride precursor has the formula

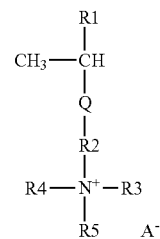

wherein R1 is H or $CH_3$; Q is —C(O)O—, —OC(O)—, or —C(O)NH—; R2 is branched or linear ($C_1$-$C_4$) alkylene; R3, R4, and R5 are independently chosen from H, $C_1$-$C_4$ linear, cyclic or branched alkyl or alkylene, or an $C_5$-$C_8$ aromatic group or alkylaromatic group, $N^+$R3R4R5 can also be a cyclic system, $A=Cr^-$.

Another embodiment of the invention pertains to the novel monomer diallyldimethylammonium acetate and its preparation. Another aspect of the invention, pertains to the novel polymer polydiallyldimethylammonium acetate and its preparation.

In still further embodiments, methods for clarifying wastewater comprise adding to the wastewater a polydiallyldimethylammonium acetate. The wastewater may, for example, be oily wastewater from the food and beverage, steel, automotive, transportation, refinery, pharmaceutical, metals, paper and pulp, chemical processing and hydrocarbon processing industries. In still further environments, methods for clarifying water comprise adding to the water a polydiallyl dimethyl ammonium acetate. The water may be raw water from lakes, streams, wells, ponds and rivers.

DETAILED DESCRIPTION

In one exemplary embodiment of the invention, a novel monomer, diallydimethyl ammonium acetate (DADMOAC) is made based upon the metathesis reaction between potassium acetate and diallyldimethylammonium chloride (DADMAC). The high solubility of DADMOAC vs. KCl forces the latter compound to be precipitated in quantitative yields. Simple filtration leads to formation of the novel monomer, (DADMOAC) and solid KCl. In another aspect of the invention, the novel monomer can be polymerized by known free radical techniques to yield polydiallyldimethylammonium acetate (PDADMOAC).

In one embodiment, the DADMOAC can be prepared by one of two similar methods. The first method involves mixing of commercially available DADMAC monomer (≈65%) with powdered potassium acetate to lead to the quantitative precipitation of KCl. Simple filtration of the resulting solution yields the DADMOAC monomer.

In an alternative synthetic route, the potassium acetate is prepared by neutralization of potassium hydroxide solution (≈50%) by acetic acid (≈99%). The resulting potassium acetate is then reacted with the DADMAC solution (≈65%) at room temperature. After about two hours, the complete precipitation of KCl is effected. The DADMOAC monomer is isolated from the precipitate by simple filtration under reduced pressure. In some experiments to date, the yield of ≈68% solution of DADMOAC is quantitative >98-99%.

One general procedure for preparing Cl⁻ free monomers and polymers from DADMAC is as follows:

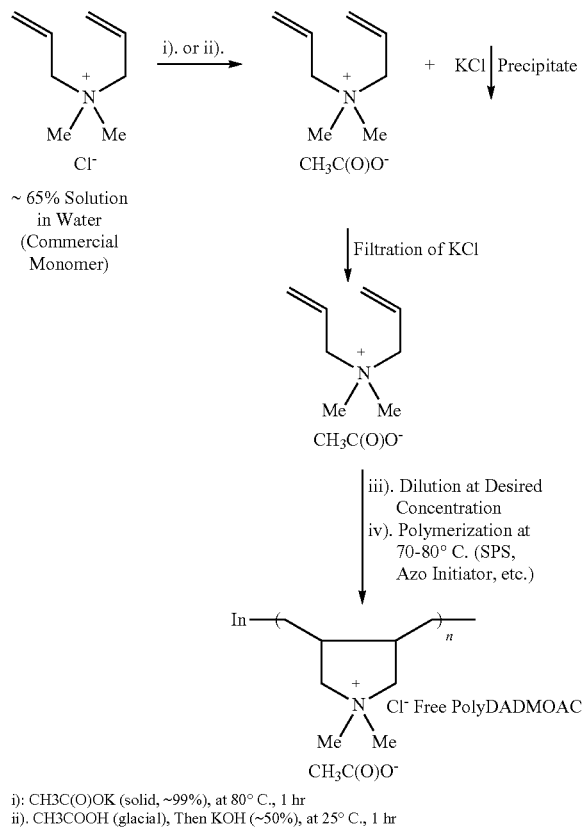

i): CH3C(O)OK (solid, ~99%), at 80° C., 1 hr
ii). CH3COOH (glacial), Then KOH (~50%), at 25° C., 1 hr Another exemplary procedure follows the route:

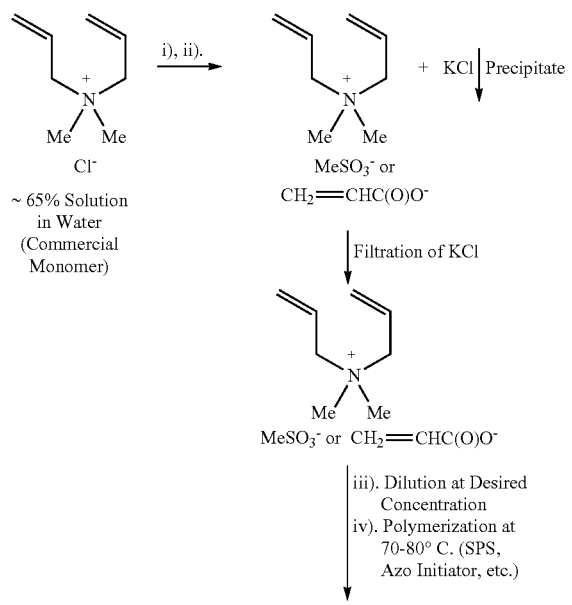

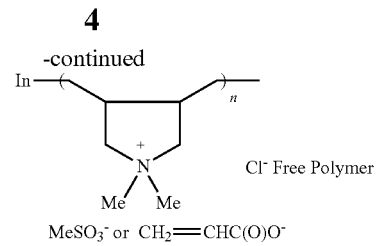

i). Methanesulfonic or Acrylic Acid,
ii). ~50% KOH solution, 1 hr, RT

The isolated monomer, or aqueous solution containing such monomer, can be polymerized by traditional free radical techniques such as those reported in U.S. Pat. No. 3,288,770, incorporated by reference herein. For example, temperature ranges for the polymerization may vary between about 0-100° C. for a period of from about 1-72 hours. The monomer concentrate in the reaction medium may be within the range of 5-70% with concentrations of between about 50-70 wt % being preferred.

Water is the generally preferred reaction solvent, but other solvents may also be employed such as methanol, ethanol, dimethyl formamide, diethyl formamide, dimethyl acetamide, acetonitrile, dimethoxyethane, etc. Catalyst (initiator) concentrations from about 0.05%-5.0% (based on monomer weight) and 0.1-1.0% may be mentioned as exemplary.

As to the initiators that may be employed, peroxide initiators such as dicumyl peroxide, t-butylhydroperoxide, acetyl peroxide, and benzoyl peroxide may be used. Azo based initiators such as azoisobutyronitrile are also effective, and persulfate initiators such as sodium or potassium persulfate may also be mentioned.

The use of an anion contributing metathesis agent such as potassium acetate to synthesize the Cl⁻ anion free quantitative monomer provides a simple and direct reaction route. As is known in the art, metathesis refers to a molecular process involving the exchange of bonds between two reacting chemical species which results in the creation of products with similar or identical bonding affinities. Here, the metathesis reaction occurs between the Cl⁻ anion and substitute anion such as the acetate ion from potassium acetate. In the reaction, the acetate replaces or substitutes for the Cl ion associated with the quaternary nitrogen compound. The resulting KCl precipitates from the reaction medium.

As used herein, the phrase "anion contributing metathesis agent" refers to a compound in which the anionic portion thereof will substitute for or replace the Cl⁻ ion from the quaternary ammonium moiety. Although potassium acetate is clearly preferred, potassium acrylate and potassium methane sulfonate may also be mentioned as exemplary anion contributing metathesis agents since, when these are employed in the reaction, the acrylate anion and methosulfonate anion replace the Cl⁻ ion from the quat.

In addition to providing replacement of the Cl⁻ anion from DADMAC type quaternary ammonium salt compounds (Quats), the reaction can be employed to substitute a more environmentally acceptable anion to a multiplicity of varying Cl containing quats. For instance, although some of the specific examples involve reaction of the popular DADMAC quat, other diallyldialkylammonium chlorides shall similarly react. (The alkyl groups may, for example, be from $C_1$-$C_6$ alkyl). Additional tests with acryloyl and acrylamido quats result is similar substitution of acrylate, methosulfate, and acetate anions for the chloride anion in precursor quats.

For example, the general metathesis reaction can be utilized to substitute anions from monomeric precursors having the formula:

Formula I

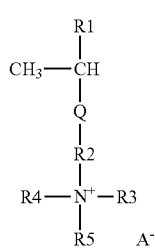

wherein R1 is H or CH$_3$; Q is —C(O)O—, —OC(O)—, or —C(O)NH—, R2 is branched or linear (C$_1$-C$_4$) alkylene; R3, R4, and R5 are independently chosen from H, C$_1$-C$_4$ linear, cyclic, or branched alkyl or alkylene, or an C$_5$-C$_8$ aromatic group or alkylaromatic group; N$^+$R3R4R5 can also be a cyclic system, A=Cl$^-$. Exemplary monomers encompassed by Formula I above include:

AETAC=2-acryloxyethyltrimethyl ammonium chloride
MAPTAC=3-(meth) acrylamidopropyl trimethyl ammonium chloride
METAC=2-methacryloxyethyltrimethyl ammonium chloride These monomers can readily be converted to acetate, methosulfate, or acrylate counter ion form.

The general procedure for preparing Cl$^-$ free monomers from Formula I type quats is as follows:

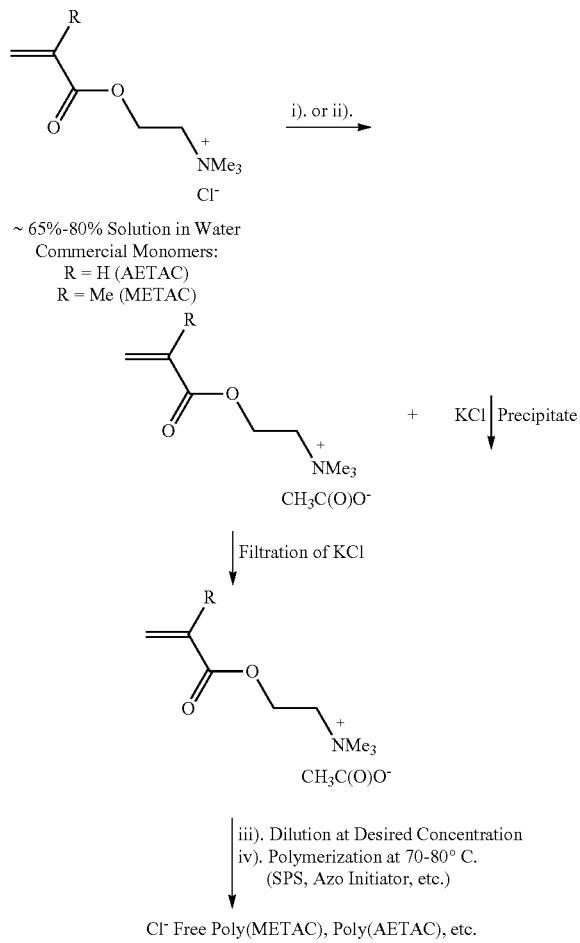

i): CH3C(O)OK (solid, ~99%), at 80° C., 1 hr
ii): CH3COOH (glacial), Then KOH (~50%), at 25° C., 1 hr The polymers produced from the chloride free quaternary ammonium salt monomers may be employed as coagulants for treating wastewater. In this regard, the polymers may be fed in an amount of from 0.5-500 ppm; 0.25-100 ppm; 0.5-75 ppm, or from 1-50 ppm to the wastewater based on one million parts of said wastewater. The wastewater is generally primary or secondary wastewater including oily wastewater from the food and beverage, steel, automotive, transportation, refinery, pharmaceutical, metals, pulp and paper, chemical processing, or hydrocarbon processing industries. The polymer may also be fed in the dosage range of 0.5-500 ppm to clarify raw water from rivers, lakes, ponds, streams, wells, and aquifers.

EXAMPLES

Example 1

Diallyldimethylammonium Acetate Monomer Preparation (DADMOAC)—Protocol A 200 g of (0.804 mol) of ≈65% commercially available diallyldimethylammonium chloride (DADMAC) and 79.49 g of potassium acetate (0.806 mol) (≈99.5%) were mixed in a chemical reaction flask. The heterogeneous mixture was heated at about 80° C. while agitated for at least 60 minutes. The resulting reaction mixture was then cooled to 25° C., and after 120 minutes, the reaction mixture was filtered under reduced pressure at 25° C.

KCl precipitate was filtered from the reaction mixture with approximately 217.1 g of DADMOAC remaining in the solution water with DADMOAC being present in an amount of ≈68% solution in water resulting in about 148.8 g (≈0.804 mol) of DADMOAC. DADMOAC yield was about 99%. 60.2 g of KCl was separated from the reaction mixture (theoretical ≈259.8 g).

30 g of DI water was added to the DADMOAC aqueous solution in order to delete the solution to about 60% actives DADMOAC. The pH of this 60% solution was about 8.34 (25° C.).

Example 2

DADMOAC Monomer Preparation—Protocol B 192.9 DADMAC (≈67.6%) solution (0.804) mole and 48.7 g (0.804 mol) glacial acetate acid were charged into a reaction flask and stirred at 25° C. In a separate flask, 51.80 g (0.804 mol) KOH pellets (≈86.9%) were mixed with 48.2 g DI water. The first reaction flask containing DADMAC and glacial acetic acid was cooled to about 15-20° C.

The KOH solution from the second flask was added to the first flask over a period of about 120 minutes with the resulting reaction mixture in the first flask subjected to intense agitation. The temperature of the reaction mixture in the first flask was carefully monitored so as not to exceed 80° C. Upon completion of the addition of the KOH solution to the first flask, this reaction mixture was then heated to about 90-100° C. in order to evaporate 62.7 g water. The reaction mixture was then cooled to 25° C. and allowed to stand at this temperature for 120 minutes. The reaction mixture was then filtered under reduced pressure in order to remove KCl. The yield of KCl salt after drying was ≈60.39 (theoretical 59.9 g), and the yield of DADMOAC solution was about 217.7 g~99% (theoretical ≈218.4 g). The resulting DADMOAC solution had a pH of about 8.95 (25° C.), and the active DADMOAC concentration in solution was ≈60% in water. 29 g of DI water was added to the DADMOAC solution in order to dilute the solution to a 60% DADMOAC actives concentration. The pH of this 60% solution was ≈8.29 (25° C.).

Example 3

Radical Polymerization of DADMOAC Monomer (≈60% in Water) Using Potassium Persulfate Initiator An aqueous solution containing 115 g DADMOAC monomer (60% solution) was charged into a reactor under agitator on condition. The solution was heated to 80° C. and sparged with nitrogen for 20-30 minutes. Potassium Persulfate (SPS) (0.5 g) was dissolved in 2.0 g of DI water in order to form an initiator solution. The initiator solution was fed to the DADMOAC solution for 120 minutes at 120° C.

Agitation of the reaction solution was continued for 60 minutes at 80° C. After addition of the initiator, a shot of 1.1 g SPS and 3.0 g DI water was prepared, mixed and sparged with nitrogen for 2-3 minutes. This additional shot of initiator was then shot fed to the reaction mixture in order to polymerize residual monomer. The reaction mixture was heated to 85° C. and maintained under agitation at this temperature for 90 minutes. After this reaction was completed, the reaction was cooled to 25° C. 54.0 g DI water was added for dilution, and the reaction mixture was then agitated for an additional 30 minutes.

The resulting polymer solution was obtained:
pH=6.61 (25° C.)
Solids=44.25%
Viscosity=1600 cps (LV3, 30 rpm @ 25° C.)
Mw (GPC)=48,600
Mw/Mn (GPC)=4.05
MW and Mn are determined by GPC using calibration based on the narrow Mw/Mn polyethyleneoxide standards.

Example 4

Radical Polymerization of DADMOAC Monomer (≈55% in Water)—SPS Initiator

An aqueous solution containing 125 g DADMOAC monomer (55% solution) was charged into a reactor under agitator on conditions. The solution was heated to 80° C. and sparged with nitrogen for 20-30 minutes. SPS (0.75 g) was dissolved in DI water (2.09) in order to provide an initiator solution. This initiator solution was fed to the DADMOAC solution over a period of 120 minutes while the reaction mixture was maintained at 120° C. with a continuous agitation. After the initiator addition was over, the reaction mixture was agitated for an additional 60 minutes at 80° C. A burnout shot of initiator solution was prepared by mixing 1.5 g SPS in 3.5 g DI water under nitrogen sparging conditions for 2-3 minutes. This burnout shot initiator was added to the reaction mixture, with the reaction mixture being heated to 85° C., under agitation, for 90 minutes. After the reaction was over, the reaction mixture was cooled to 25° C. Dilution water in an amount of 40.0 g DI was added while the mixture was agitated for an additional 30 minutes.

The resulting polymer solution was obtained:
pH=6.45 (25° C.)
Solids=43.50%
Viscosity=1200 cps (LV3, 30 rpm @ 25° C.)
Mw (GPC)=39,000
Mw/Mn (GPC)=3.98
Mw and Mn are determined by GPC using calibration based on the narrow Mw/Mn polyethyleneoxide standards.

Example 5

Monomer Synthesis

([2-(methacryloyl)ethyl]-trimethylammonium acrylate)—METAC/Acrylate 221.30 g (0.847 mol) of METAC (≈79.5% solution in water) and 61.6 g (0.847 mol) acrylic acid (≈99%) were charged into a reaction flask. The resulting solution was agitated for 10 minutes and cooled down at 10-15° C. 54.7 g (0.847 mol) KOH (≈86.9%) was dissolved in 33.3 g DI water with the resulting KOH solution cooled to about 20° C. The KOH solution was added to the METAC/acrylic acid solution over a period of 120 minutes while the temperature was maintained below 40° C. to avoid spontaneous polymerization. After termination of the KOH solution addition, the mixture was stirred continuously for 120 minutes at 25° C. KCl formed as a solid precipitate and was separated from the reaction medium by filtering under reduced pressure. The yield of KCl was 66.7 g (theoretical 63.10 g) with the yield of METAC/acrylate being 297.36 g≈96.7% (theoretical 307.8 g).

The pH of the METAC/Acrylate solution was 6.67 (25° C.), and the solids content of the METAC/acrylate in solution was about 66.9%.

Example 6

Monomer Synthesis

([2-(Acryloyl)ethyl]-trimethylammonium (acrylate)—AETAC/Acrylate 216.0 g (0.847 mol) AETAC (≈75.9% solution in water) and 61.6 g (0.847 mol) Acrylic Acid (≈99%) were charged into a reaction flask. The resulting solution was agitated for 10 minutes and cooled down at 10-15° C. In a separate flask, 54.7 g (0.847 mol) KOH (≈86.9%) was mixed in 33.3 g DI water. The KOH solution was cooled to 20° C. and then added to the AETAC/Acrylic Acid mixture over a period of 120 minutes. Temperature of the reaction mixture was maintained below 40° C. to avoid spontaneous polymerization. After termination of the KOH solution, the reaction mixture was continuously stirred for a period of 120 minutes while the temperature was maintained at 25° C. KCl formed as a solid precipitate and was separated from the reaction mixture under reduced pressure to yield AETAC/Acrylate in solution. The yield of KCl was 69.60 g (theoretical 63.10 g) with the yield of AETAC/Acrylate solution being 279.05 g, ≈92.2% (theoretical 302.50 g). The pH of the AETAC/Acrylate solution was 6.61 (25° C.) with a solids content of about 69.50% AETAC/acrylate in solution.

Example 7

In order to demonstrate the efficacy of the DADMOAC polymers in reducing turbidity in sample wastewaters, the following tests were undertaken.

Jar tests were undertaken to evaluate water clarification efficacy of the coagulants. 600 ml beakers were filled with the sample wastewater. The desired coagulant dosage was then added to each beaker with the beakers stirred with paddles first at 100 rpm and then 35 rpm for a total stirring time of 7 minutes. The beakers were allowed to settle for 5 and then 30 ml of supernatant from each beaker was removed via syringe. The supernatant samples were then measured with a HACH 2100 AN Tubidimeter set to the NTU (nephlelometric turbidity unit) measurement mode.

Results are shown in Table 7.1.

TABLE 7.1

Standard LNVA River Water Standard Jar Tests
Raw NTU = 93
pH = 7(+1-0.2)

| Treatment | ppm active | | | | | | | | | | |
|---|---|---|---|---|---|---|---|---|---|---|---|
| | 0 | 1 | 2 | 3 | 4 | 5 | 6 | 7 | 8 | 9 | 10 |
| C-1 | 93 | 53.3 | 47.2 | 16.1 | 4.47 | 2.71 | 3.53 | — | 4.76 | — | 5.77 |
| A-1 | 93 | 64.8 | 62 | 23.4 | 3.88 | 2.47 | 3.02 | — | 4.50 | — | 6.29 |
| A-2 | 93 | 71 | 52.2 | 15.6 | 5.81 | 3.32 | 3.26 | — | 5.46 | — | 6.03 |
| A-3 | 93 | 79.2 | 71.2 | 27.1 | 19.6 | 5.45 | 3.98 | — | 3.32 | — | 4.37 |

C-1 = polyDADMAC
A-1 = polyDADMOAC—made in accordance with Example 4; molecular weight 39,100 Mw/Mn = 3.98
A-2 = polyDADMOAC—made in accordance with Example 3; molecular weight 48,600 Mw/Mn 4.05
A-3 = polyDADMOAC—made in accordance with Example 3 except that initiator feed time was 90 minutes, Mw = 44,900 Mw/Mn 3.90

While typical embodiments have been set forth for the purpose of illustration, the foregoing descriptions should not be deemed to be a limitation on the scope of the appended claims. It is apparent that numerous other forms and modifications of this invention will occur to one skilled in the art. The appended claims and these embodiments should be construed to cover all such obvious forms and modifications that are within the true spirit and scope of the present invention.

The invention claimed is:

1. A method for clarifying water comprising adding to said water a coagulant, said coagulant being polydiallyldimethylammonium acetate (PDADMOAC) prepared using a diallyldimethylammonium acetate (DADMOAC) monomer formed by:
reacting diallyldimethylammonium chloride and an anion contributing metathesis agent in an aqueous solution to yield a precipitate and a diallyldimethylammonium anion, and removing said precipitate from said solution; wherein said anion contributing metathesis agent is potassium acetate and said precipitate is KCl.

2. A method as recited in claim 1 wherein said water is raw, untreated water from a lake, river, pond, stream or aquifer.

3. A method as recited in claim 1 wherein said water is wastewater.

4. A method as recited in claim 1 wherein about 0.5-75 ppm of said PDADMOAC is added to said wastewater.

5. A method as recited in claim 4 wherein about 1 to about 50 ppm of said PDADMOAC is added to said wastewater.

6. A method as recited in claim 3 wherein said wastewater is oily wastewater from food and beverage, steel, automotive, transportation, refinery, pharmaceutical, metals, paper and pulp, chemical processing, and hydrocarbon processing industries.

7. A method as recited in claim 6 wherein said PDADMOAC has a molecular weight of between about 5,000 to 2,000,000.

8. The method of claim 1, wherein said coagulant is added to said water in the amount of about 0.25-500 ppm based upon one million parts of said water.

\* \* \* \* \*